(12) United States Patent
Gallant et al.

(10) Patent No.: US 9,388,519 B1
(45) Date of Patent: *Jul. 12, 2016

(54) NEEDLING FIBROUS WEBS

(71) Applicants: Christopher M. Gallant, Nottingham, NH (US); James R. Barker, Francestown, NH (US); Gregory R. Kopanski, Manchester, NH (US); David Erick Fuller, Goffstown, NH (US)

(72) Inventors: Christopher M. Gallant, Nottingham, NH (US); James R. Barker, Francestown, NH (US); Gregory R. Kopanski, Manchester, NH (US); David Erick Fuller, Goffstown, NH (US)

(73) Assignee: Velcro BVBA (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/972,234

(22) Filed: Dec. 17, 2015

Related U.S. Application Data

(63) Continuation of application No. 14/610,625, filed on Jan. 30, 2015.

(51) Int. Cl.
| | | |
|---|---|---|
| *D04H 1/46* | (2012.01) |
| *D04H 1/485* | (2012.01) |
| *D04H 1/541* | (2012.01) |
| *D04H 1/498* | (2012.01) |
| *D04H 1/558* | (2012.01) |
| *A44B 18/00* | (2006.01) |
| *A61F 13/62* | (2006.01) |

(52) U.S. Cl.
CPC ............ *D04H 1/485* (2013.01); *A44B 18/0011* (2013.01); *A61F 13/627* (2013.01); *D04H 1/46* (2013.01); *D04H 1/498* (2013.01); *D04H 1/541* (2013.01); *D04H 1/558* (2013.01)

(58) Field of Classification Search
CPC ........... D04H 1/46; D04H 1/48; D04H 1/485; D04H 1/541; D04H 1/558; D04H 18/02; A44B 18/0011; A61F 13/627
See application file for complete search history.

(56) References Cited

U.S. PATENT DOCUMENTS

| | | |
|---|---|---|
| 2,706,324 A | 4/1955 | Cogovan |
| 3,950,587 A | 4/1976 | Colijn et al. |
| 4,010,302 A | 3/1977 | Anderson et al. |
| 4,154,889 A | 5/1979 | Platt |
| 4,258,094 A | 3/1981 | Benedyk |
| 4,324,824 A | 4/1982 | Narens et al. |

(Continued)

FOREIGN PATENT DOCUMENTS

| | | |
|---|---|---|
| DE | 3006805 A1 | 9/1981 |
| EP | 211564 B1 | 2/1992 |

(Continued)

OTHER PUBLICATIONS

International Search Report for PCT/EP2016/051911 dated May 13, 2016.

*Primary Examiner* — Michael Tolin
(74) *Attorney, Agent, or Firm* — Fish & Richardson P.C.

(57) ABSTRACT

Methods for forming a touch fastening material are described as including: providing a lengthwise-incoherent layer of staple fibers supported directly on a bed of bristle tips of a brush; needling the layer of staple fibers by cycling needles through the layer of staple fibers and into the brush; then, while the needled layer of staple fibers remains supported on the brush, fusing portions of the staple fibers by at least partially melting resin of the fibers disposed outside the brush; and then pulling the layer of fibers from the brush as a lengthwise-coherent touch fastening material having exposed fastening loops pulled from between the brush bristles.

10 Claims, 10 Drawing Sheets

(56) References Cited

U.S. PATENT DOCUMENTS

| | | |
|---|---|---|
| 4,379,189 A | 4/1983 | Platt |
| 4,439,476 A | 3/1984 | Guild |
| 5,216,790 A | 6/1993 | Eschenbach |
| 5,265,954 A | 11/1993 | Keil |
| 5,630,896 A | 5/1997 | Corbin et al. |
| 5,891,547 A | 4/1999 | Lawless |
| 6,086,984 A | 7/2000 | DiMaggio et al. |
| 6,329,016 B1 | 12/2001 | Shepard et al. |
| 6,642,160 B1 | 11/2003 | Takahashi |
| 6,783,834 B2 | 8/2004 | Shepard et al. |
| 6,893,525 B1 | 5/2005 | Schmidt et al. |
| 7,117,571 B2 | 10/2006 | Dilo |
| 7,156,937 B2 | 1/2007 | Provost et al. |
| 7,465,366 B2 | 12/2008 | Provost et al. |
| 7,547,469 B2 | 6/2009 | Provost et al. |
| 7,562,426 B2 | 7/2009 | Barker et al. |
| 8,500,940 B2 | 8/2013 | Shepard et al. |
| 8,673,097 B2 | 3/2014 | Barker et al. |
| 8,753,459 B2 | 6/2014 | Provost et al. |
| 2002/0160143 A1 | 10/2002 | Shepard et al. |
| 2004/0157036 A1 | 8/2004 | Provost et al. |
| 2005/0196581 A1 | 9/2005 | Provost et al. |
| 2005/0208259 A1 | 9/2005 | Provost et al. |
| 2005/0217092 A1* | 10/2005 | Barker ............... A44B 18/0011 28/106 |
| 2006/0225258 A1 | 10/2006 | Barker et al. |
| 2008/0113152 A1 | 5/2008 | Provost et al. |
| 2011/0253289 A1 | 10/2011 | Shepard |
| 2013/0052399 A1 | 2/2013 | Barker |
| 2013/0052403 A1 | 2/2013 | Barker et al. |

FOREIGN PATENT DOCUMENTS

| | | |
|---|---|---|
| EP | 0780505 A2 | 6/1997 |
| EP | 1276348 A1 | 1/2003 |
| EP | 1279348 A1 | 1/2003 |
| GB | 1228431 A | 4/1971 |
| JP | 7171011 A | 7/1995 |
| JP | 09-317 | 1/1997 |
| WO | WO0180680 A1 | 11/2001 |

* cited by examiner

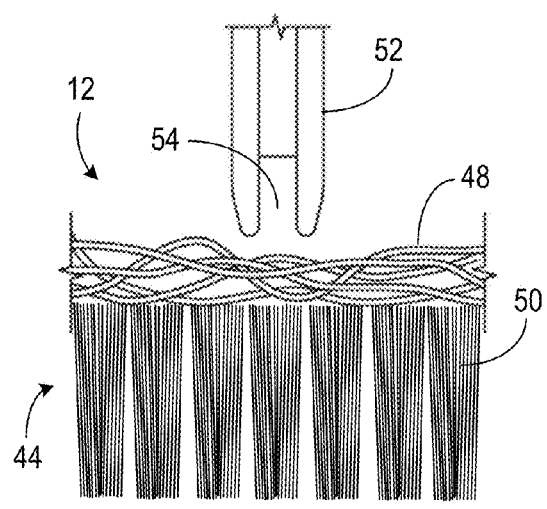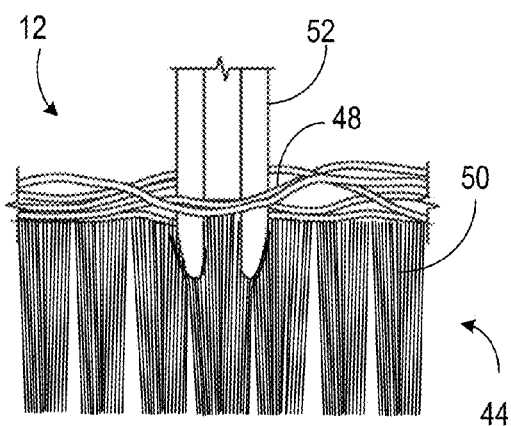
FIG. 2A　　　　　　　FIG. 2B
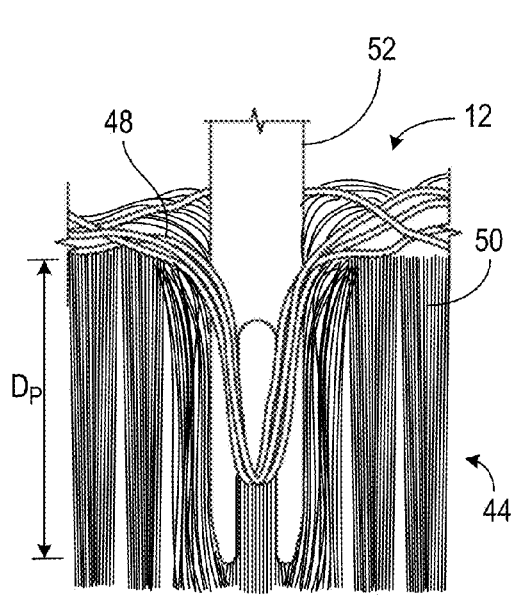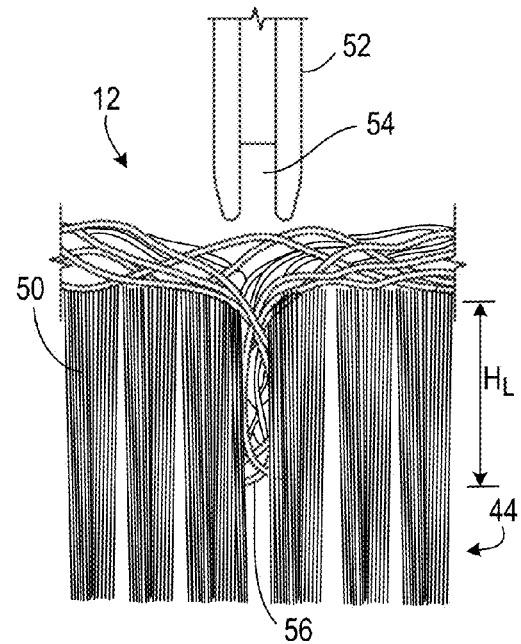
FIG. 2C　　　　　　　FIG. 2D

NEEDLING FIBROUS WEBS

This is a continuation of U.S. Ser. No. 14/610,625, filed on Jan. 30, 2015, entitled Needling Fibrous Webs. The disclosure of this prior application is hereby incorporated by reference in its entirety and is therefore considered part of the disclosure of this application.

TECHNICAL FIELD

This invention relates to methods of making sheet-form loop products, particularly by needling carded fibrous webs, and products produced thereby.

BACKGROUND

Touch fasteners are particularly desirable as fastening systems for lightweight, disposable garments, such as diapers. In an effort to provide a cost-effective loop material, some have recommended various alternatives to weaving or knitting, such as by needling a lightweight layer of fibers to form a light non-woven material that can then be stretched to achieve even lighter basis weight and cost efficiency, with the loop structures anchored by various binding methods, and subsequently adhered to a substrate. U.S. Pat. No. 6,329,016 teaches one such method, for example.

Materials with lower unit costs and better performance are desired. Reducing fiber content can lower cost, but can also affect overall performance or load-carrying capacity of the loop material, as well as the dimensional stability and handling efficiency of the loop product. Also, choice of fiber material is often compromised by a need for the loop material to be weld-compatible with a substrate (e.g., an outer layer of a diaper) to which the loop material is to be permanently bonded, and by the load-bearing requirements of the fastener loop fibers.

Various methods of bonding fibers to underlying substrates have also been taught, for forming touch fasteners and other loop-bearing materials.

SUMMARY

In one aspect of the present disclosure, a method of forming a touch fastening material includes: providing a lengthwise-incoherent layer of staple fibers supported directly on a bed of bristle tips of a brush, the total weight of fibers supported on the brush being less than about 60 grams per square meter; needling the layer of staple fibers by cycling needles through the layer of staple fibers and into the brush, such that the needles carry loops of fibers of the layer into spaces between bristles of the brush; then, while the needled layer of staple fibers remains supported on the brush, with the loops of the fibers extending between bristles of the brush, fusing portions of the staple fibers by at least partially melting resin of the fibers disposed outside the brush; and then pulling the layer of fibers from the brush as a lengthwise-coherent touch fastening material having exposed fastening loops pulled from between the brush bristles.

In this context, by "lengthwise-incoherent" we mean that the layer of fibers has little to no dimensional stability in the lengthwise direction, and will fall apart if even a linear meter of the layer is suspended under its own weight from a transverse edge. Conversely, "lengthwise-coherent" means that the touch fastening material has sufficient dimensional stability that at least a linear meter of the material is suspended under its own weight from a transverse edge. With respect to a particular application, a "lengthwise-coherent" material should be able to be removed (e.g., pulled) from the brush without falling apart.

In some examples, the fibers have a nominal tenacity of at least 1.1 grams per denier. In some applications, the fibers have a nominal tenacity of at least 2.5 grams per denier. In some cases, the fibers include bicomponent fibers including two resins of differing softening temperatures. In some applications, a plurality of the bicomponent fibers include a core of resin of higher softening temperature than resin of a sheath about the core, and at least partially melting resin of the fibers includes melting the sheath. In some examples, at least partially melting resin of the fibers includes melting the sheath of one or more bicomponent fibers, while leaving the core of the bicomponent fibers substantially intact.

In some implementations, as provided on the brush, the total weight of fibers of the layer is less than about 40 grams per square meter.

In some applications, the fibers have a denier of between about 1 and 20.

In some embodiments, providing the lengthwise-incoherent layer of staple fibers includes carding staple fibers and then transferring the carded fibers onto the brush. In some applications, the lengthwise-incoherent layer of staple fibers is transferred onto the brush as a longitudinally continuous layer, such that the fibers are oriented to extend primarily along a length of the layer.

In some examples, the lengthwise-incoherent layer of staple fibers is provided supported on a brush having a bristle density of about 380 bristles per square centimeter.

In some cases, the lengthwise-incoherent layer of staple fibers is provided supported on bristles having a nominal diameter of between about 4 and 15 times a nominal diameter of the staple fibers.

In some implementations, the lengthwise-incoherent layer of staple fibers is provided supported directly on rounded bristle tips.

In some applications, needling the layer of staple fibers includes cycling fork needles through the layer of staple fibers.

In some embodiments, needling the layer of staple fibers includes penetrating the needles through the layer of fibers to a distance of between 1 and 10 millimeters into the brush.

In some examples, needling the layer of staple fibers includes needling the layer of staple fibers with a needling density of between 40 and 320 penetrations per square centimeter.

In some cases, fusing portions of the staple fibers includes fusing such that the lengthwise-coherent touch fastening material as pulled from the brush has a permeability of at least 500 feet$^3$/feet$^2$/sec.

In some implementations, fusing portions of the staple fibers includes applying heat and pressure to the fibers remaining outside the brush.

In some applications, the heat and pressure is applied by a surface maintained in contact with the fibers while the fibers are transported by the brush.

In some embodiments, the needling and fusing is performed such that the lengthwise-coherent touch fastening material pulled from the brush has substantially the same overall width as the layer of staple fibers provided on the brush.

In some examples, the needling and fusing is performed such that the lengthwise-coherent touch fastening material pulled from the brush has a fastening surface featuring visually discrete fibers extending between bases of the loops.

In some cases, the lengthwise-incoherent layer of staple fibers is continually provided on the brush as a longitudinally continuous layer, and transported by the brush while needled and fused.

In some implementations, the brush is in the form of a conveyor belt maintained to travel along a linear path during the needling and fusing, and the lengthwise-coherent touch fastening material is pulled from the brush.

In some applications, the lengthwise-coherent touch fastening material, as pulled from the brush, consists essentially of material of the layer of staple fibers as provided on the bed of bristle tips of the brush.

The details of one or more embodiments of the invention are set forth in the accompa-nying drawings and the description below. Other features, objects, and advantages of the invention will be apparent from the description and drawings, and from the claims.

DESCRIPTION OF DRAWINGS

FIGS. 2A-2D are progressive diagrammatic side views detailing a needing stage of the process of FIG. 1.

DETAILED DESCRIPTION

Figure 1:
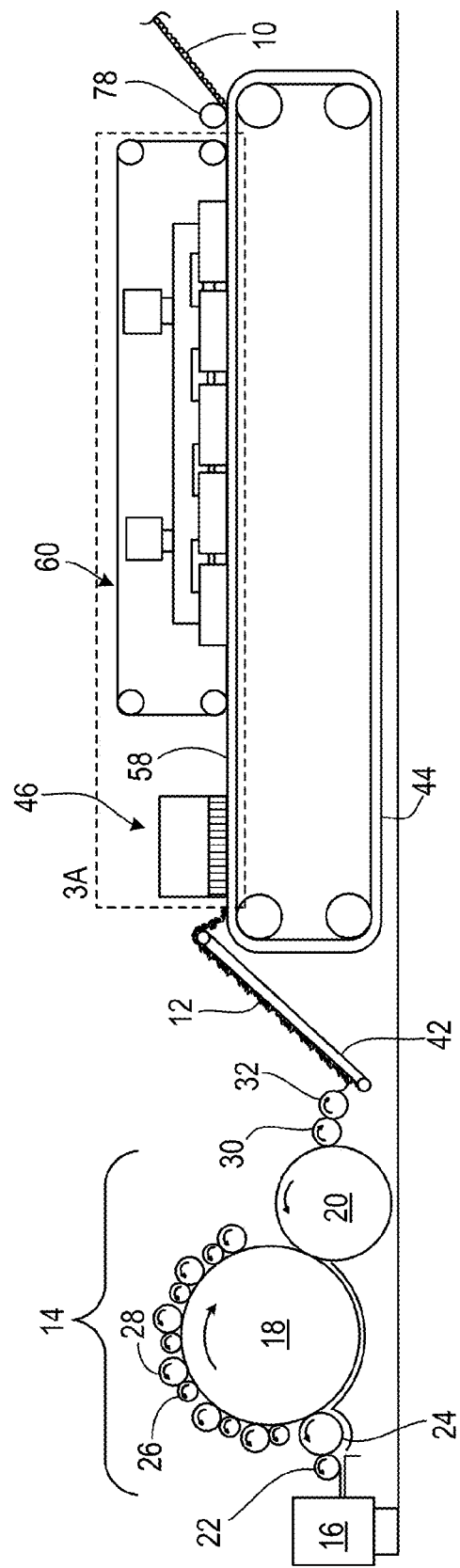
FIG. 1 is a diagrammatic plan view of a process for forming loop product.

FIG. 1 illustrates a machine and process for producing an inexpensive touch fastener loop product 10. Beginning at the upper left end of FIG. 1, a carded web of fibers 12 is created by an initial carding stage. As shown, weighed portions of staple fibers are fed to a carding station 14 by a card feeder 16. In this example, carding station 14 includes a 50-inch main cylinder 18 and a 27-inch doffer 20. The card feedroll drive includes a 2.25-inch feed roll 22 and a 9-inch lickerin roll 26 that transfers the fibers to main cylinder 18. An alternating pattern of 3-inch stripper rolls 26 and 6-inch worker rolls 28 is distributed along the peripheral surface of main cylinder 18. In this example, carding station 14 includes six worker-stripper pairs, with the stripper rolls driven at a surface speed two to three times faster than the worker rolls. Doffer 20 transfers carded web 12 to a 6-inch condenser roll 30, and a take-off roll 32 deposits the carded web on a conveyor 42.

While the configuration shown and described herein is illustrative of an example carding station for providing lengthwise-incoherent fibers suitable for use in conjunction with various techniques presently disclosed, it should be understood that other methods of providing such lengthwise-incoherent fibers are also contemplated (e.g., alternative carding and air lay configurations).

During carding, the fibers are separated and combed into a cloth-like continuous layer consisting primarily of parallel fibers oriented to extend primarily along a length of the layer (carded web 12). The mat has virtually no strength when pulled in any direction because the fibers have been disentangled and are otherwise untethered. Thus, carded web 12 emerges from the carding station 14 as a "lengthwise-incoherent" layer of staple fibers, having little to no dimensional stability in the lengthwise direction, and will pull apart if attempted to be lifted from the conveyor.

In some embodiments, suitable fibers for forming the loop product 10 are drawn and crimped fibers, 1.5 to 6 denier, of about 1-inch (about 2.5 centimeters) to 4-inch (about 10 centimeters) staple length. Various synthetic or natural fibers may be employed. For example, in some applications, combinations of natural fibers, such as wool and cotton, and synthetic, thermally fusible fibers, may provide sufficient loop strength. Presently, however, thermoplastic staple fibers which have substantial tenacity are preferred for making thin, low-cost loop product that has good closure performance when paired with very small molded hooks. Suitable thermoplastic materials may include polymers, such as polyesters, polyamides, polyolefins (e.g., polypropylene and polyethylene), acrylics, and rayon, as well as blends and copolymers of such polymers. In some embodiments, the carded web includes one or more multicomponent fibers. Some multicomponent fibers are bicomponent fibers feature an outer sheath and an inner core. Suitable bicomponent fibers may include bicomponent polyester fibers and bicomponent polyethylene/polyester fibers. In some implementations, it may be particularly advantageous to employ bicomponent fibers having a broad bonding window, where the inner core material has a much higher melting point that the outer sheath material. In some embodiments, a blend of different types of fibers may be used. For example, a suitable fiber blend may include at least one "binder fiber" (i.e., a fiber having a particularly low melt temperature) and one or more "loop fibers" having relatively higher melt temperature and tenacity suitable for engagement with male fastener elements. For example, the polyethylene sheath of a suitable bicomponent fiber may have a melting temperature of about 266° F. (about 130° C.) and the polyester core may have a melting temperature of about 485° F. (about 252° C.). For a product having some electrical conductivity, a small percentage of metal fibers may be added. For instance, loop products of up to about 5 to 10 percent fine metal fiber, for example, may be advantageously employed for grounding or other electrical applications. In some embodiments, the composition of a fiber blend may include at least 50 percent binder fiber.

Loop fibers with tenacity values of at least 1.1 grams per denier have been found to provide good closure performance, and fibers with a tenacity of at least 5 or more grams per denier (preferably even 8 or more grams per denier) are even more preferred in many instances. In general terms for a loop-limited closure, the higher the loop tenacity, the stronger the closure. For many applications, particularly products where the hook-and-loop components will be engaged and disengaged more than once ("cycled"), it is desirable that the loops have relatively high strength so that they do not break or tear when the fastener product is disengaged. Loop breakage causes the loop material to have a "fuzzy," damaged appearance, and widespread breakage can deleteriously effect re-engagement of the fastener. Loop strength impacts closure performance and is proportional to fiber tenacity and denier.

Fibers having a fiber titer of at least 1.5 to 6 denier and a tenacity of at least 1 to 7 grams/denier, provide sufficient loop strength for many applications. Where higher loop strength is required, fiber denier, tenacity, or both, may be increased. The loop fiber denier should be chosen with the hook size in mind, with lower denier fibers typically selected for use with smaller hooks. In applications for use with larger hooks, larger fiber titer and/or higher tenacity may be employed.

Referring again to FIG. 1, carded web 12, in its lengthwise-incoherent state, is carried up conveyor 42 and deposited on a brush apron 44. In some embodiments, brush apron 44 is provided in the form of a continuous belt supporting a dense bed of upstanding flexible bristles. As shown, brush apron 44 is maintained to travel at a constant line speed along a linear path while carrying carded web 12 through various stations of the manufacturing process. In this example, brush apron 44 initially carries the dispensed carded web 12 to a needling station 46, where the carded web is repeatedly needle-punched. The needles may be guided through a stripper plate above the fibers, and draw small pouches of fibers through the carded web to form loops on the opposite side. During needling, carded web 12 is supported directly on the bristles of brush apron 44 (as shown in FIGS. 2A-2D), which moves with the carded web through needling station 46. In some embodiments, needling station 46 needles carded web 12 with an overall penetration density of about 40 to 160 punches per square centimeter.

In some embodiments, needling station 46 may be provided in the form of a "structuring loom" configured to subject the fibers of carded web 12 to a random velour process. Thus, the needles penetrate a moving bed of bristles arranged in an array (brush apron 44). In some implementations, the needling station may feature a double-beam, random-velour needle loom. In a particular implementation, needle beams are fitted with needle boards having a density of 7500 needles/meter. In this implementation, the needle loom was fitted with 40 gauge, 2.5 inch needles cycled at a stroke amplitude of 40 millimeters and a stroke frequency of 2100 strokes per minute. In some implementations, the needling station may feature two consecutive double-beam looms.

In some embodiments, brush apron 44 may have a nominal bristle density of about 2500 bristles per square inch (about 380 bristles per square centimeter). The bristles are each about 0.008 inch (0.2 millimeter) in diameter and about 20-25 millimeters long, and are preferably straight with rounded tips. In some embodiments, brush apron 44 includes a plurality of discrete brush segments 45 (see FIG. 3A) secured to aluminum slats driven by a continuous belt over a supporting steel deck. Alternatively, in some alternative embodiments, the bristles of brush apron 44 are directly attached to the continuous belt. The bristles may be formed of any suitable material, for example 6/12 nylon. Suitable brushes may be purchased commercially and retrofitted onto suitable looms. Generally, the brush apron moves at the desired line speed.

FIGS. 2A through 2D sequentially illustrate the formation of a loop structure by a suitable needling process, such as may be performed at needling station 46. Initially, carded web 12 is conveyed to the needling station by brush apron 44, with the individual fibers 48 of the carded web carried directly on a bed of brush bristles 50 (FIG. 2A). As a fork needle 52 enters carded web 12 (FIG. 2B), some individual fibers 48 will be captured in the cavity 54 between the leading prongs of the forked end of the needle. As needle 52 "punches" through the carded web, these captured fibers 48 are drawn down with the needle into the bed of brush bristles 50. As shown, carded web 12 remains generally supported on brush apron 44 through this process. Thus, the penetrating needle 52 laterally displaces local brush bristles 50 as it intrudes upon brush apron 44. As needle 52 continues to penetrate (FIG. 2C) through brush bristles 50, tension is applied to the captured fibers 48, drawing them tightly around the penetration point. In this example, a total penetration depth "$D_p$" of up to about 10 millimeters, as measured from the top surface of brush apron 44, was found to provide a well-formed loop structure without overly stretching fibers in the remaining web. Excessive penetration depth can draw loop-forming fibers from earlier-formed tufts, resulting in a less robust loop field. Penetration depths of 2 to 10 millimeters may also be implemented in this example, with 2 millimeters to 4 millimeters penetration being presently preferred. When needle 52 is retracted from the bristle bed (FIG. 2D), the portions of the captured fibers 48 carried through brush bristles 50 remain in place having the form of a plurality of individual loops 56 effectively clamped between previously displaced—now recovered—bristles. With a punch depth of 2.5 mm, the resulting loop formation has an overall height "HL" of about 0.040 to 0.060 inch (1 to 1.5 millimeters), measured optically prior to compression or spooling and while the loop product is free of any load, for engagement with the size of male fastener elements commonly employed on disposable garments and such. It should be understood that additional needle types may be used; for example, felting needles or crown needles.

Advance of the carded web per needle stroke is limited due to a number of constraints, including needle deflection and potential needle breakage. Thus, it may be difficult to accommodate increases in line speed and obtain an economical throughput by adjusting the advance per stroke. As a result, the alignment of the unbonded fibers may be disturbed due to the travel of the web on the brush apron during penetration of the needle. For applications in which this effect is undesirable, an elliptical needling technique (such as described in U.S. Pat. No. 7,465,366 the entirety of which is incorporated herein by reference), or similar, can be used to reduce or eliminate relative movement between the web and the penetrating needles. Using elliptical needling, it may be possible to obtain line speeds of 60 mpm (meters/minute) or greater, e.g., 120 mpm. Such speeds may be obtained with minimal disturbance of the unbonded fibers.

For needling longitudinally discontinuous regions of the material, such as to create discrete loop regions, the needle boards can be populated with needles only in discrete regions, and the needling action paused while the material is indexed through the loom between adjacent loop regions. Effective pausing of the needling action can be accomplished by altering the penetration depth of the needles during needling, including to needling depths at which the needles do not penetrate the carded web. Such needle looms are available from Autefa Solutions in Austria, for example. Alternatively, means can be implemented to selectively activate smaller banks of needles within the loom according to a control sequence that causes the banks to be activated only when and where loop structures are desired. Lanes of loops can be formed by a needle loom with lanes of needles separated by wide, needle-free lanes.

Figure 3A:
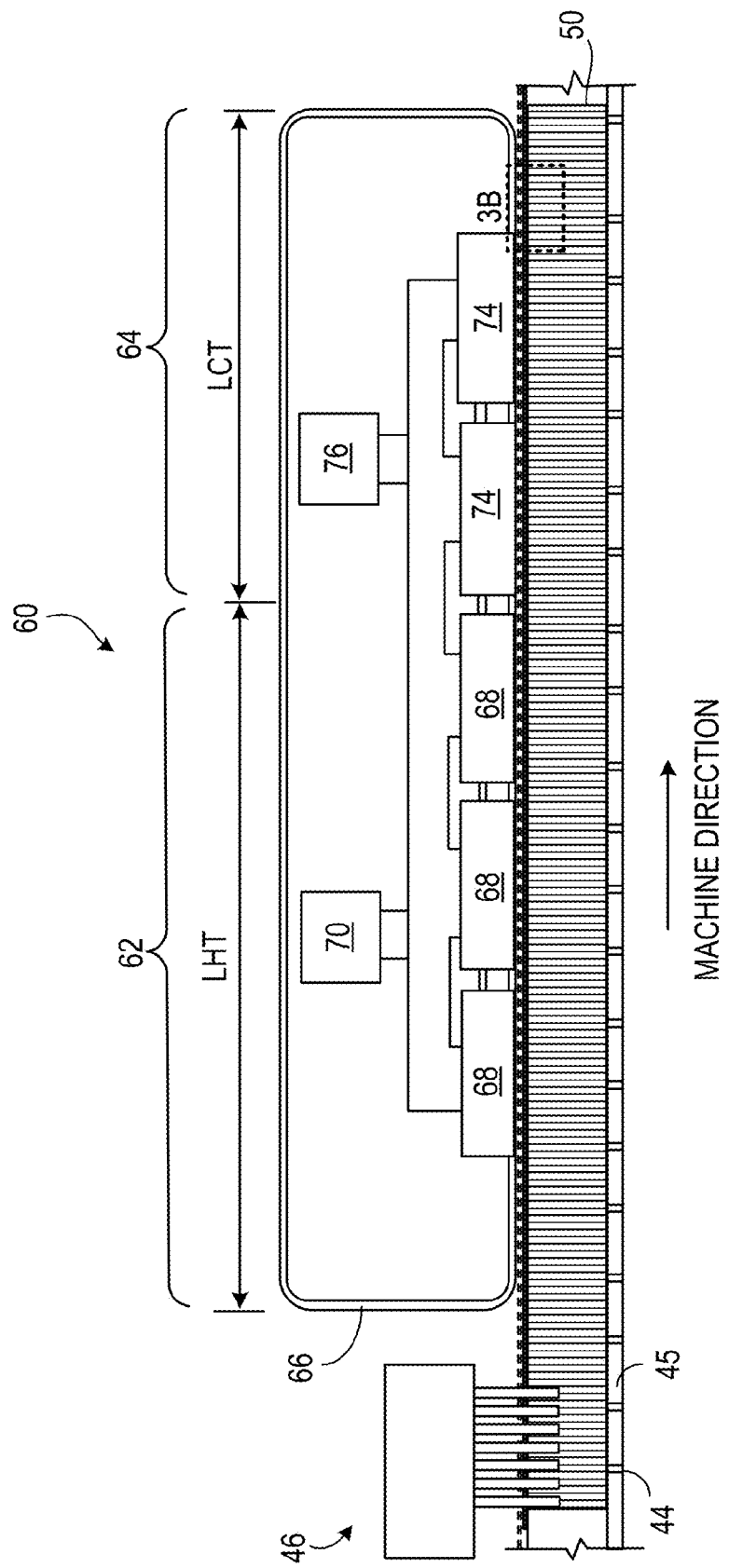
FIG. 3A is diagrammatic plan view of a portion of the process of FIG. 1 marked 3A.

Referring back to FIG. 1, the needled product 58 leaves needling station 46 in an unbonded state, and proceeds to a bonding station 60 while the loops 56 of fibers remain engaged within the bristle bed of brush apron 44. At bonding station 60, portions of fibers exposed on the surface of the bristle bed, opposite the loops held by the bristles of brush apron 44, are at least partially fused to create a dimensionally stable base layer of the product. As illustrated in FIG. 3A, bonding station 60 includes a heating section 62 and a cooling section 64 integrated by a single, continuous conveyor belt 66, for example a Teflon® belt or a belt with similar heat-transfer and release properties. Heating section 62 includes a bank of heating modules 68 operated by a controller 70. Similarly, cooling section 64 includes a bank of cooling modules 74 operated by a controller 76. Conveyor belt 66 rides against the respective heating and cooling modules 68, 74 while simultaneously contacting needled product 58 to facilitate a bonding process with appropriate heating/cooling under pressure. During the bonding process the surfaces in contact with each side of the product (e.g., conveyor belt 66 and brush apron 44) move at the same longitudinal speed, avoiding relative motion at the fibers. Thus, conveyor belt 66 is operated to match the line speed of brush apron 44 to avoid disturbing the needled fibers with relative motion.

Figure 3B:
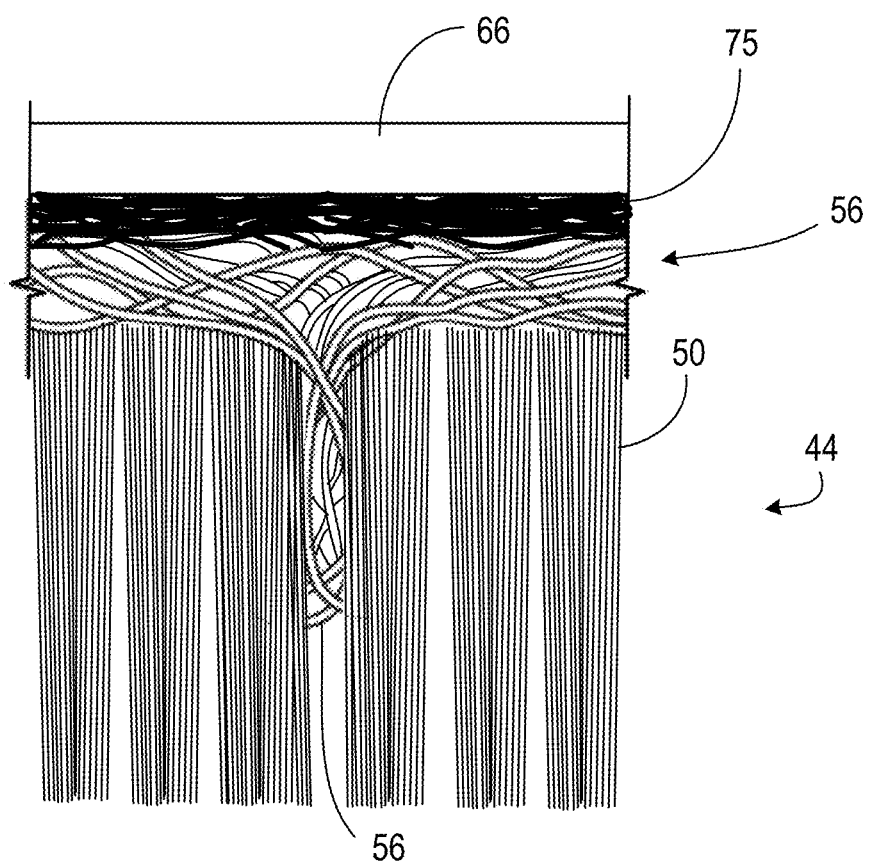
FIG. 3B is a diagrammatic side view of a bonding stage of the process of FIG. 3A marked 3B.

FIG. 3B provides an example illustration of needled product 58 sandwiched between conveyor belt 66 and the bristles 50 of brush apron 44. As shown, heat applied to the exposed fibers outside the brush apron 44 creates a partially melted and fused fibrous web 75, while the loops 56 of fibers secured between the bristles remain substantially unbonded. In some implementations, there may be a transition zone between the denser, fused layer on the backside of the needled product 58 and the unfused layer on the front resting against the brush apron 44 where there is gradually less melting and fusing of the staple fibers. The characteristics of this transition zone (e.g., degree of melting and fusing, thickness, etc.) may vary with different process parameters. In some implementations, when bicomponent fibers are used, the bonding parameters may be selected so that only the outer sheaths of the bicomponent fibers are melted. Thus, the sheaths of the bicomponent fibers act as an adhesive agent to bond the fibers together, while the cores of the fibers remain substantially intact, maintaining their integrity. Further, in some examples, the melting and reforming of the outer sheaths at or near the base of the loops tends to support the cores of the fibers in an upright position when the loop structures are pulled from the brush apron.

Returning to FIG. 3A, in some embodiments, the heating and cooling modules 68, 74 may be operated by the respective controllers 70, 76 individually or in subgroups of staged heating/cooling zones along the length and/or width of the heating and cooling conveyor belts 66, 72. In some embodiments, heating modules 68 are operated such that the heating zones provide a steadily increasing temperature profile in the "machine direction" (i.e. the direction of travel of the needled product as it is carried through the heating section on the brush apron 44). The progressive temperature profile may create the effect of a gradual "heat soak" that steadily heats the exposed fibers (at least) up to an "activation temperature" (e.g., a melting or softening temperature of the outer sheath of a bicomponent fiber) at which the fibers begin to fuse together under relatively light pressure applied by the heating conveyor belt. As one example, to achieve fusing at an activation temperature of 300° F., the following heat profile provided in Table 1 may be used:

TABLE 1

| Heating Zone | Temperature |
| --- | --- |
| Heating Zone 1 | 125° F. (about 52° C.) |
| Heating Zone 2 | 200° F. (about 93° C.) |
| Heating Zone 3 | 250° F. (about 121° C.) |
| Heating Zone 4 | 300° F. (about 149° C.) |
| Heating Zone 5 | 300° F. (about 149° C.) |
| Heating Zone 6 | 300° F. (about 149° C.) |
| Heating Zone 7 | 200° F. (about 93° C.) |

In the illustrated configuration, the bonding pressure exerted by the conveyor belt may be restricted to a relatively low level in order to avoid damage to the delicate needled product and the supporting bristles of the brush apron. The progressive heat soak achieved by light pressure contact with the conveyor belt over a relatively long dwell time (which may be achieved by providing a relatively lengthy heating section and/or a slower line speed) may provide consistent melting and amalgamation of the exposed fibers, which, after cooling, produces a cohesive and relatively flat fused web 75 (see FIG. 3B). This process configuration may also yield mitigating effects on curl and/or shrinkage in the cross-machine direction (widthwise) of the product.

In a particular example, the heating section may be configured having a heating tunnel length ($L_{HT}$) of about 3.5 meters, with 20 heating modules operated to create 5 staged temperature zones along the length of the conveyor belt and three staged temperature zones along the 1.6 meter width of the conveyor belt. The heating modules may be operated to create temperature zones ranging from about 70° F. to about 400° F. The line speed of the brush apron may be about 20 meters/minute to provide a dwell time in the heating section of about 11 seconds. Further, in this example, the cooling section was configured having a cooling tunnel length ($L_{CT}$) of about 1.5 meters, with 10 cooling modules. The cooling modules may be operated to create a temperature zones of about 35° F. to about 70° F.

Figure 4:
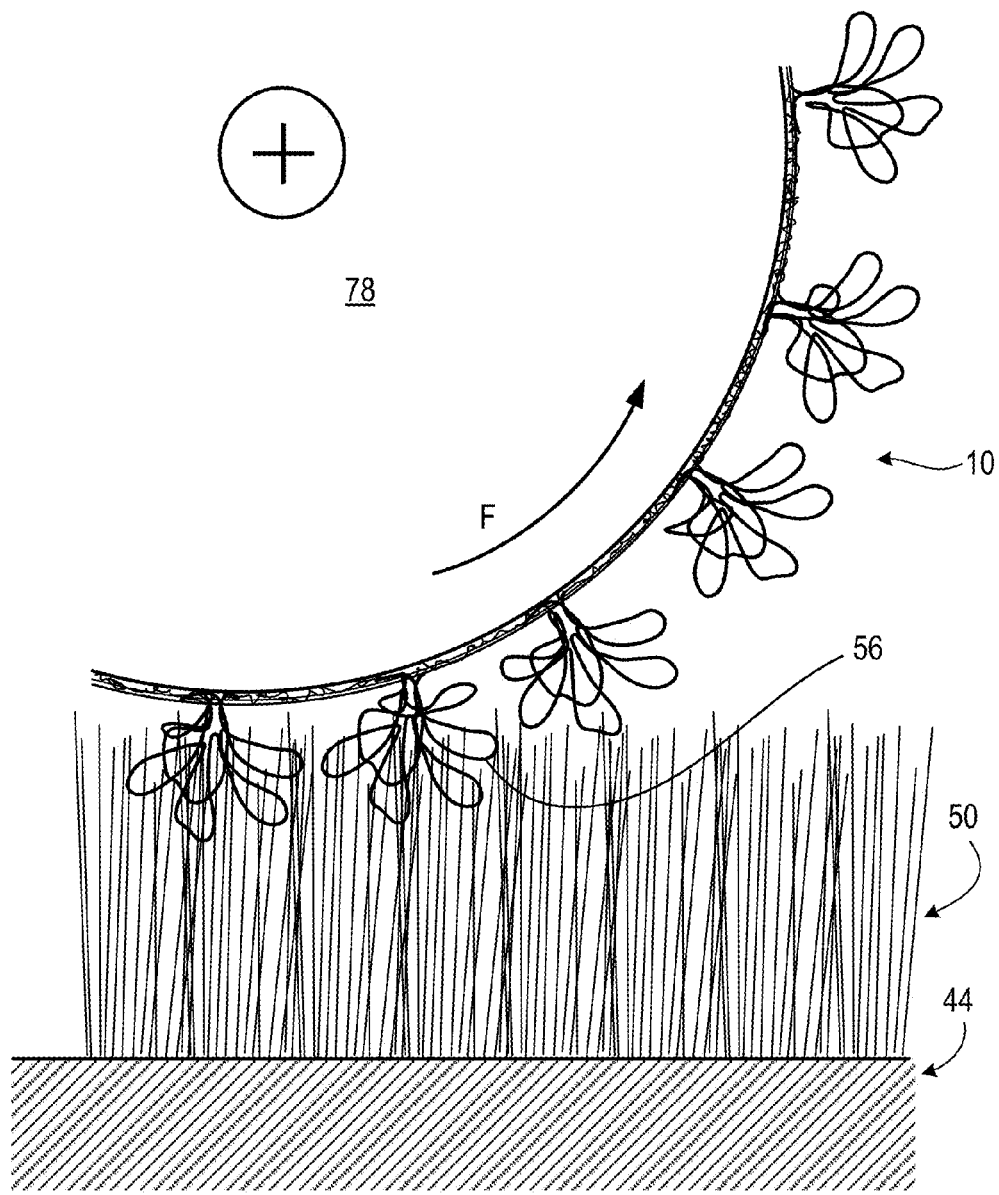
FIG. 4 is a diagrammatic side view of an example process for removing a needle-punched loop product from a supporting brush apron.

Referring back to FIG. 1, the loop product 10 leaves the bonding station 60 as a lengthwise-coherent sheet-form article having sufficient dimensional stability to be removed from brush apron 44 via tension applied by a stripper roll 78, which pulls the loops 56 of fibers from the bed brush bristles. Removed from brush apron 44, loop product 10 features a fastening layer having a plurality of exposed fastening loops extending from an underlying fused web. FIG. 4 illustrates how the loop product 10 may be pulled by stripper roll 78 with a tension force (F) while brush apron 44 remains flat to achieve a continuous release of the entrapped loops 56 from bristles 50.

Figure 5:
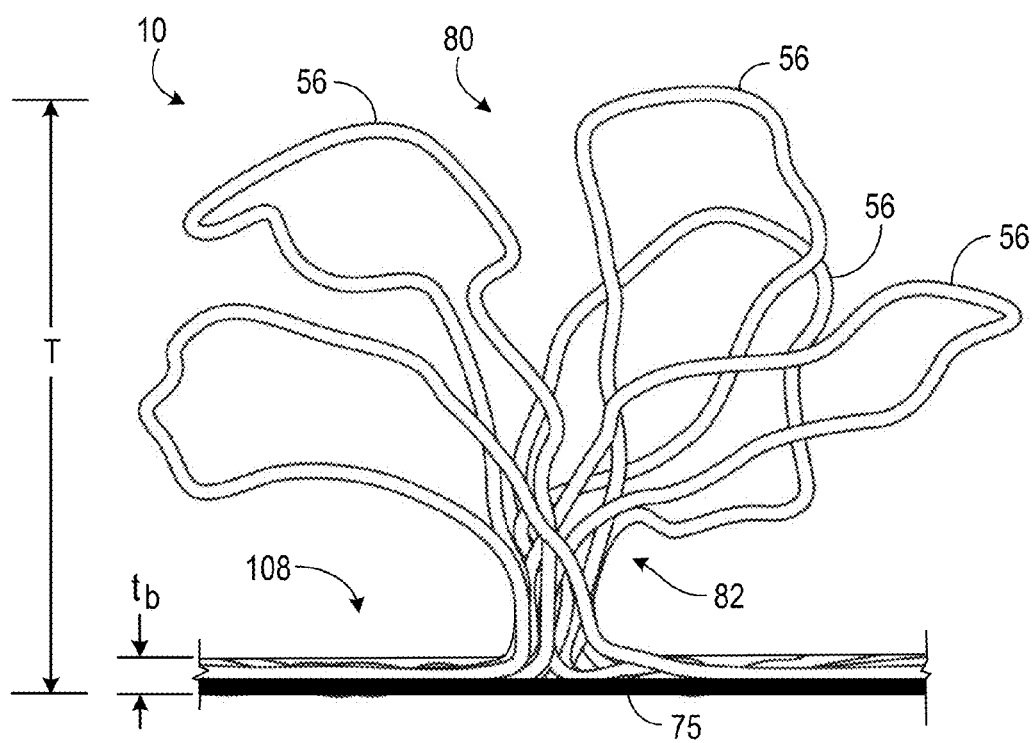
FIG. 5 is a highly enlarged diagrammatic side view of a loop structure formed by process of FIG. 1.

FIG. 5 is an enlarged view of a loop structure 80 containing multiple loops 56 of individual fibers extending from a common trunk 82 extending from a web 75 of fused fibers, as formed by the above-described process. As shown, loops 56 stand proud of the web 75, available for engagement with a mating hook product, due at least in part to the vertical stiffness of trunk 82 of each formation, which is provided by the anchoring of the fibers at the web. Preferably, the web is fused such that each loop fiber is bonded at multiple points to other fibers within the web, to provide sufficient resistance to loop pull-out during fastening uses, and to provide sufficient peel strength and shear strength. Further, as noted above, the needling process tends to draw the fibers taught around the point of penetration, which creates the stiffness in the trunk when the opposing ends of the loop fibers are fused within the web. This vertical stiffness acts to resist permanent crushing or flattening of the loop structures, which can occur when the loop material is spooled or when the finished product to which the loop material is later joined is compressed for packaging. Resiliency of the trunk 82, especially at its juncture with web 75, enables structures 80 that have been "toppled" by heavy crush loads to right themselves when the load is removed. The various loops 56 of structure 80 extend to different heights from web 75, which is also believed to promote fastener performance. As each structure 80 is formed at a penetration site during needling, the density and location of the individual structures are very controllable. Preferably, there is sufficient distance between adjacent structures so as to enable good penetration of the field of formations by a field of mating male fastener elements (not shown). Each of the loops 56 is of a staple fiber whose ends are fused to surrounding fibers of web 75, such that the loops are each structurally capable of hook engagement.

Figure 6:
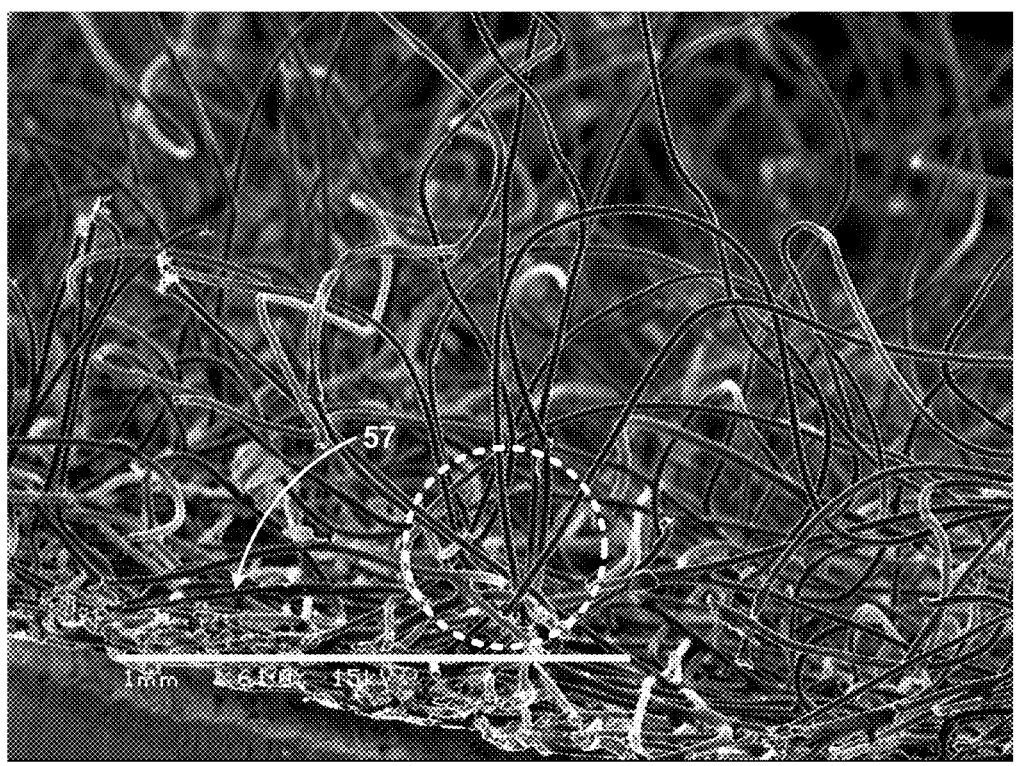
FIG. 6 is a photograph of a loop material in accordance with one or more embodiments of the present disclosure.

FIG. 6 is an enlarged photograph of a loop product formed by an implementation of the above described process. The view is taken toward an edge of the loop product and centered about a particular loop structure for increased visibility of both the upstanding loops and the underlying web of fused fibers. The fused web is clearly distinguishable from the common trunk of the loop structure (marked with a dashed line) from which multiple loops of individual fibers extend. As illustrated by the photograph, the product provides a high-density field of hook-engageable loop fibers supported on a very thin non-woven web. As is further discernable from the photograph, the outer fastening surface from which the loop fibers extend features a multitude of visually discrete fibers 57 extending between the base of the loops at the trunk of each structure. Thus, the loop product's fastening surface provides a cloth-like appearance desired in many applications involving wearable garments.

Because the entire loop product 10 is manufactured solely from staple fibers, it can be manufactured having high air permeability, low thickness and low weight with good closure performance characteristics. In some embodiments, web 75 can have a thickness "$t_b$" (see FIG. 5) of only about 0.015 inch (0.381 millimeter) or less, preferably less than about 0.010 inch (0.254 millimeter), and even as low as about 0.006 inch (0.152 millimeter) in some cases. The finished loop product 10 may have an overall thickness "T" of less than about 0.4 inch (10 millimeters), preferably less than about 0.16 inch (4 millimeters). The overall width of loop product 10 may be approximately the same overall width as the layer of staple fibers provided on the brush (i.e., not exhibiting significant signs of shrinkage). The overall weight of loop product 10, may be as low as 0.5 ounces per square yard (17 grams per square meter). In some embodiments, loop product 10 has a Frazier air permeability of at least 500 feet$^3$/feet$^2$/sec. In some embodiments, loop product 10 has a peel strength of 650 grams force per inch width, and a shear strength of at least about 8,000 grams force per square inch, when tested with HTH725 hook available from Velcro USA in accordance with test methods under ASTM D5170-98 and ASTM D5169-98.

In addition to loop tenacity and loop strength (discussed above) that are determined by fiber selection, closure performance is dependent on the density and uniformity of the loop structures over the surface area of the loop product. The techniques described above may be particularly advantageous in this regard compared to other known processes where a carded web of staple fibers is supported on a carrier sheet during needling. As a result, we have found that the presently described techniques yield a superior conversion rate of needle penetrations to "functional loops" (e.g., loop structures 80 that are suitable for engagement with male fastener elements) per unit area of the needle-punched loop product, which corresponds to increased density and uniformity. Thus, in some implementations, the loop product resulting from the above-described techniques can offer comparable or superior closure performance with lower tenacity and/or lower denier staple fibers. Therefore, loop product 10 can provide a good balance of low cost, light weight and good closure performance.

In a particular implementation, a loop product manufactured in accordance with the above-described techniques was measured to have an overall thickness of approximately 0.055 inch and a basis weight of about 32 grams per square meter (about 0.94 ounces per square yard). This loop product exhibited the following performance characteristics summarized in Table 2:

TABLE 2

| | |
|---|---|
| Peel Strength (Test with HTH725 under ASTM D5170-98) | 700 gram-force/inch (about 275 gram-force/centimeter) |
| Shear Strength (Test with HTH725 under ASTM D5169-98) | 8,686 gram-force/inch$^2$ (about 1,346 gram-force/centimeter$^2$) |
| Air Permeability | 784 feet$^3$/feet$^2$/sec |
| Break Strength - Machine Direction | 5.8 pounds-force (about 25.8 Newtons) |
| Percent Elongation - Machine Direction | 51% |
| Break Strength - Cross Machine Direction | 1.1 pounds-force (about 4.9 Newtons) |
| Percent Elongation - Cross Machine Direction | 60% |

Figure 7A:
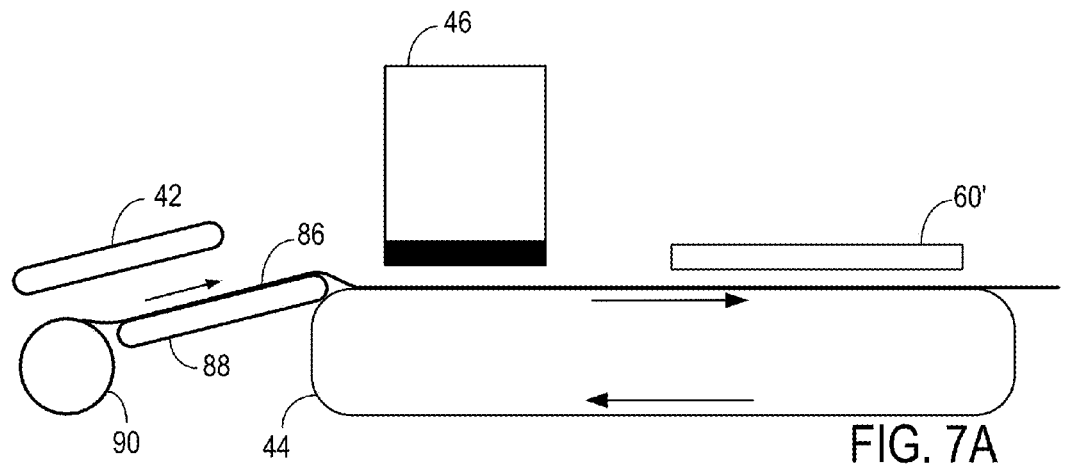
FIGS. 7A-7C are diagrammatic plan views of a startup/shutdown process that may be integrated with the process of FIG. 1.
Figure 7B:
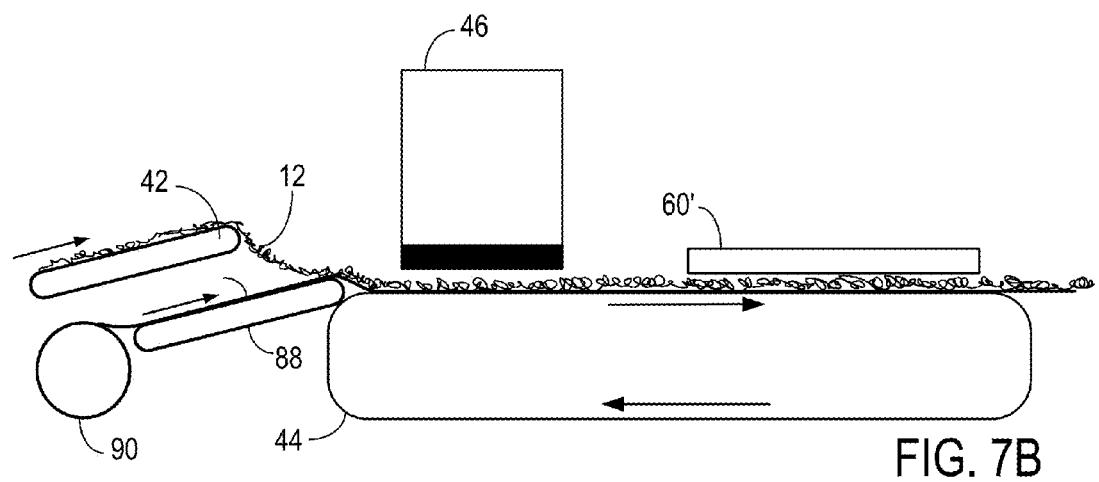
Figure 7C:
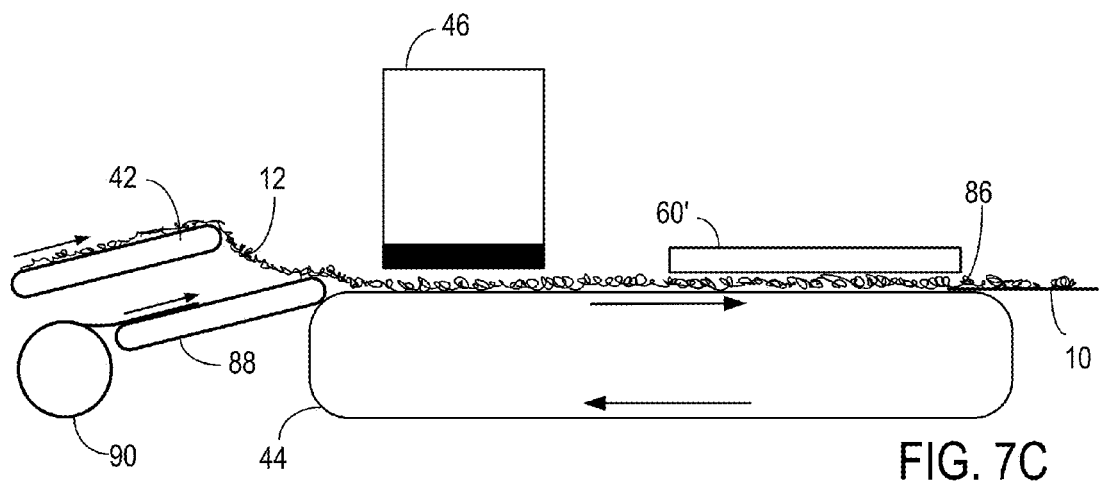

FIGS. 7A-7C illustrate a startup/shutdown machine configuration and process sequence that may be incorporated with one or more of the techniques described above. In particular, the illustrated and described process is advantageous in that it may inhibit or prevent unbonded staple fibers from clogging the bristles of the brush apron during startup and shutdown of the manufacturing line.

Initially at startup, a carrier web 86 (e.g., an inexpensive scrim fabric) is fed onto a scrim conveyor 88 from a spool 90 and deposited on the traveling brush apron 44 (FIG. 7A). At this point, before any carded fiber is introduced, needling station 46 is activated. Bonding station 60' remains inactivated. Next, the lengthwise-incoherent carded web 12 is deposited on top of the carrier web 86 via conveyor 42 (FIG. 7B). Thus, the carrier web effectively shields the brush apron from the contact with the loose, unbonded fiber of the carded web. Bonding station 60' is now activated, and the line runs in this fashion until the heating and cooling sections become fully operational to achieve satisfactory fusing of the staple fibers. Once the heating and cooling sections of bonding station 60' are fully operational—as may be evidenced by an acceptable fusing of carded web 12 to carrier web 86—the carrier web 86 is severed upstream of the of brush apron 44 (FIG. 7C) and allowed to feed through the machine. Once the tail end of carrier web 86 has run through the manufacturing line, carded web 12 is deposited directly on brush apron 44 and production of loop product 10 is commenced. As previously noted, the above-described sequence can be adapted to facilitate shutdown of the manufacturing line—e.g., by reversing the activation sequence. For example, a suitable shutdown sequence may include: reintroducing the carrier web beneath the carded web, then deactivating the bonding station and needling station in sequence.

Figure 8A:
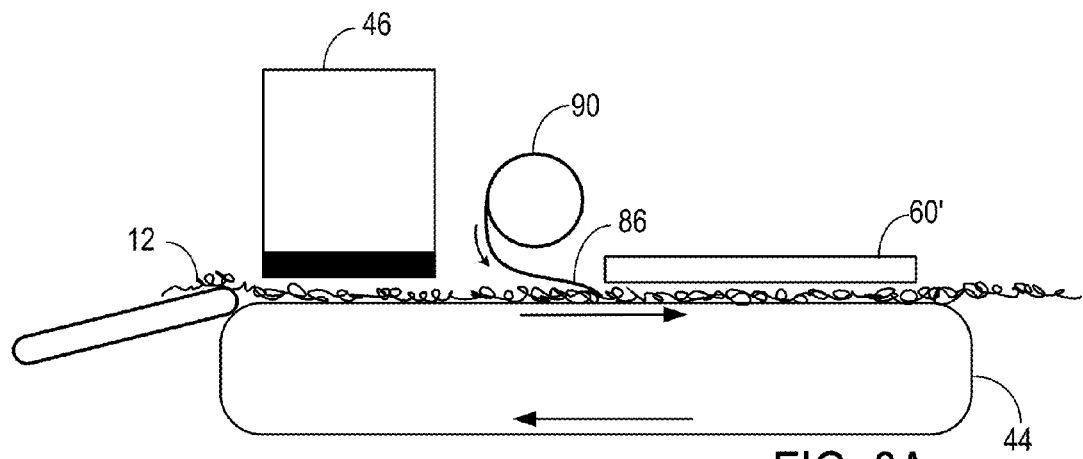
FIGS. 8A-8C are diagrammatic plan views of a brush-cleaning process that may be integrated with the process of FIG. 1.
Figure 8B:
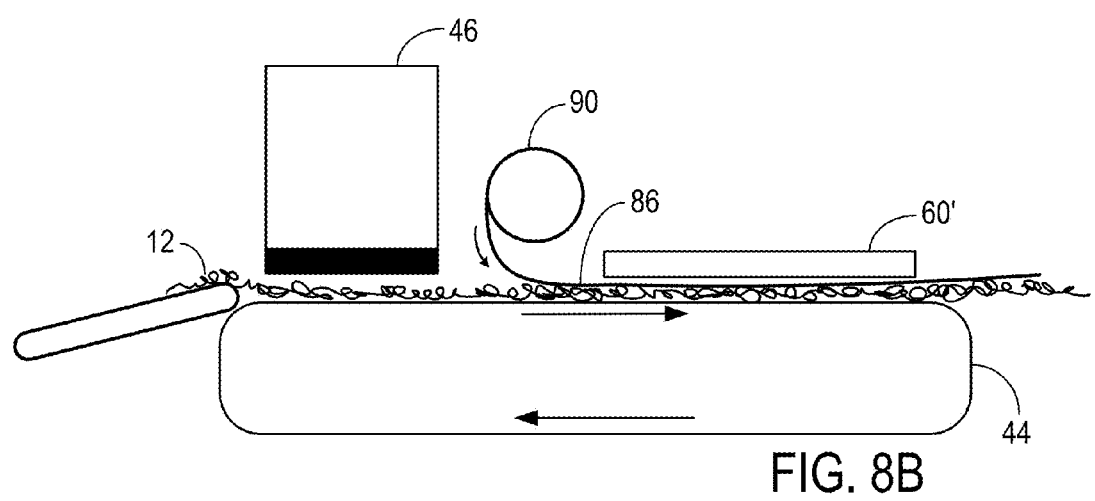
Figure 8C:
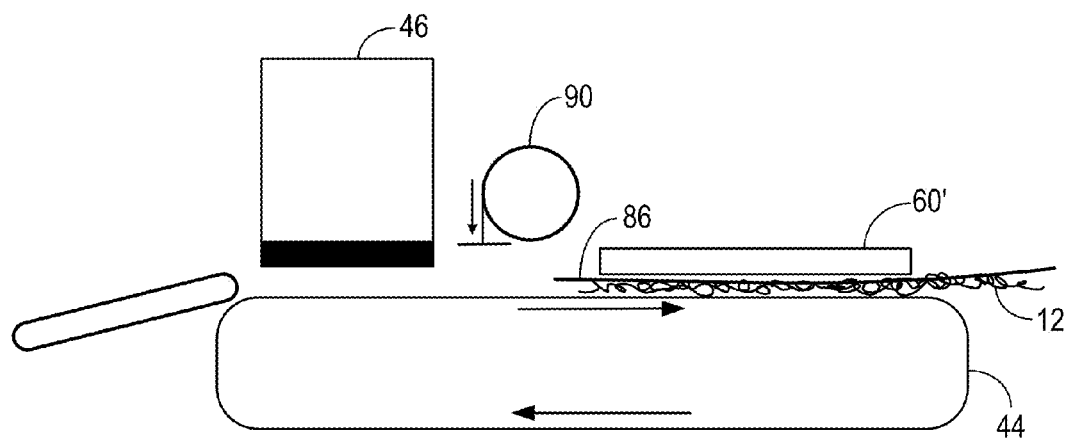

FIGS. 8A-8C illustrate a brush-cleaning machine configuration and process sequence that may be incorporated with one or more of the techniques described above. This example process is advantageous in that it may facilitate the removal of unbonded staple fibers embedded in the bristles of the brush apron. This brush-cleaning sequence may be employed during production or prior to shutdown. Initially, carrier web 86 is deposited on top of carded web 12 by spool 90 as brush apron 44 remains in motion (FIG. 8A). At this point, needling station 46 and bonding 60' remain activated. Next, in anticipation of shutdown, needling station 46 is deactivated and dispensing of carded web 12 is ceased (FIG. 8B). Bonding station 60' fuses the remains of carded web 12 to carrier web 86. Subsequently the carrier web is stripped from the brush, such as by passing the carrier web over a stripper roll (not shown), thereby pulling the remaining carded web fibers out of the brush. Carrier web 86 feeding is ceased and the carrier web is severed behind the tail end of carded web 12 while bonding station 60' remains activated, to facilitate the fiber clearing process (FIG. 8C). Bonding station 60' can be deactivated after any remaining portion of carrier web 86 passes through the manufacturing line. In some embodiments, the above-described brush cleaning sequence may be performed without deactivating the needling and evacuation stations and without ceasing dispensation of the carded web. Thus, as previously mentioned, the brush cleaning can be conducted during full operation of the manufacturing line. Further still, in some examples, a similar technique can be used to alter the process illustrated in FIG. 1 by introducing carrier web 86 to form a permanent backing layer on the loop product 10. For instance, the carrier web may be provided in the form of a thin, non-porous backing film to form a substantially impermeable laminated loop product.

Figure 9:
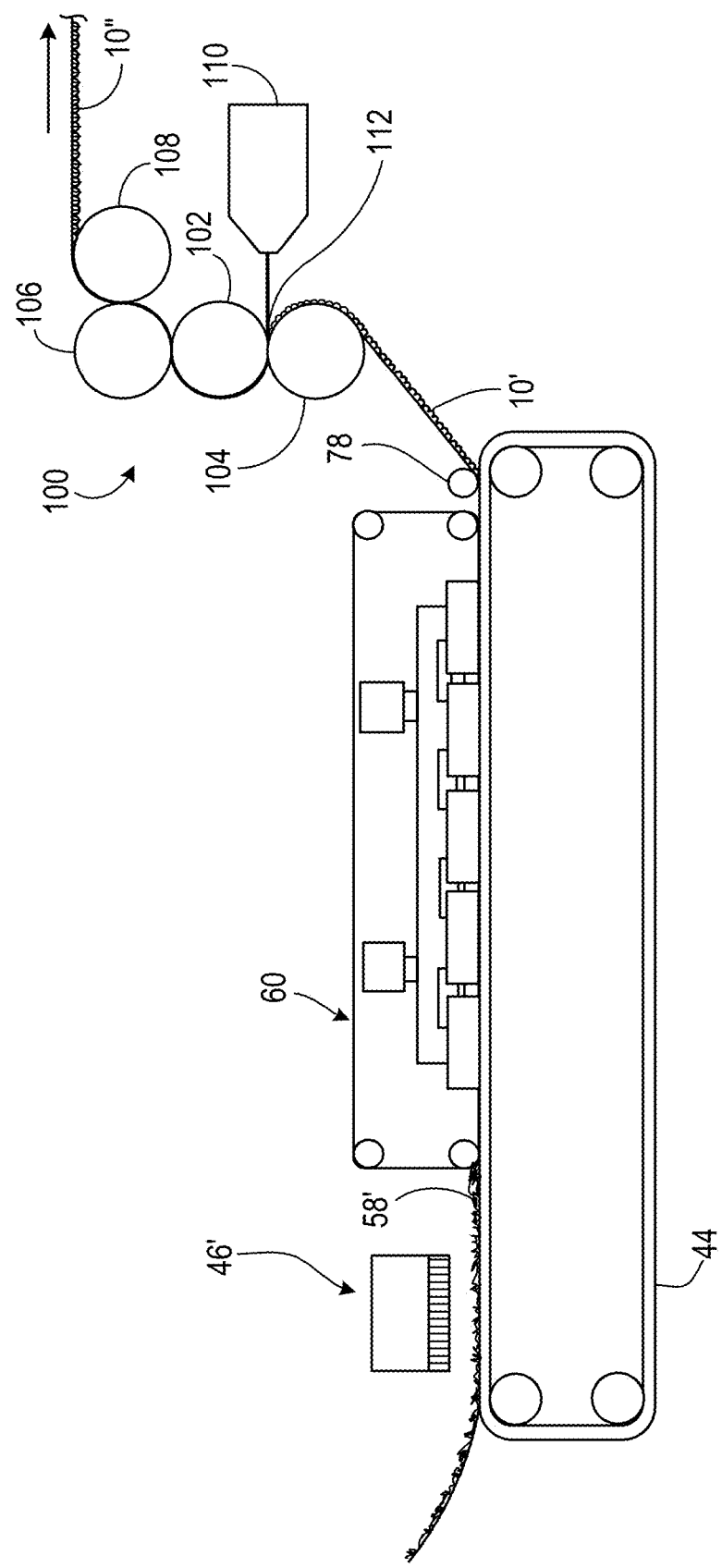
FIG. 9 is a diagrammatic plan view of a process for forming a fastener product having both hook and loop fastening features.

FIG. 9 illustrates an adaptation of the machine and process described above with respect to FIG. 1 to produce a touch fastening product 10" having both hooks and loops. In this example, carded fiber 12 is deposited on brush apron 44 and introduced to a needling station 46' configured to form a needled product 58' having one more discrete lanes of loops. For example, as noted above, needling station 46' may be provided in the form of a needling loom designed to selectively activate different banks of needles along the desired lanes or a needling loom with lanes of needles separated by wide, needle-free lanes. As shown, needled product 58' is carried on brush apron 44 to bonding station 60, where the fused web is formed to provide a lengthwise-coherent loop product 10'. Loop product 10' is removed from brush apron 44 by stripper roll 78 and fed to a roll molding apparatus 100 of the general type shown in U.S. Pat. No. 4,872,243 issued to Fischer, the details of which are hereby incorporated by reference.

Roll molding apparatus 100 includes a temperature-controlled cylindrical mold roll 102, a temperature-controlled cylindrical pressure roll 104, a takeoff roll 106, a guide roll 108, and an extruder die 110. Mold roll 102 has one or more lanes of small mold cavities in its peripheral surface. The mold cavities are shaped to form male hook fastener elements. Mold roll 102 and pressure roll 104 are counter-rotating rolls that define a calender nip 112. Loop product 10' is fed into calender nip 112 with the fused web surface riding along pressure roll 104 and its loop surface exposed to mold roll 102. Extruder die 110 extrudes moldable resin in one or more moldable sheets led into calender nip 112 between loop product 10' and mold roll 102. The pressure of calender nip 112 forces the moldable resin sheet into the mold cavities of mold roll 102 where it is cooled and solidified. Tension applied by takeoff roll 106 pulls the solidified fastener elements from the mold cavities, and guide roll 108 directs the fastener product 10" having parallel lanes of loops and hooks in the downstream direction of the manufacturing line towards a product spool or one or more post processing station. In an alternative arrangement (not shown), the loop side of the fused loop product is fed into the molding station with the fused side facing the mold roll, such that the resulting product has exposed loops on one broad surface and exposed hooks extending from an opposite broad surface, so as to make a product of the configuration sold by Velcro USA, Inc. under the trade name ONE-WRAP.

Further, it should be noted that other suitable techniques for processing loop product 10' could be utilized, such as laying lanes of adhesive or molding features other than hooks, without departing from the scope of the present disclosure. Further still, in some embodiments, the presently described techniques may be employed using a loop product that is not provided with discrete loop-free lanes. In this case, the heat and pressure of the molding process can integrate the loops together with the molded resin.

While a number of examples have been described for illustration purposes, the foregoing description is not intended to limit the scope of the invention, which is defined by the scope of the appended claims. There are and will be other examples and modifications within the scope of the following claims.

What is claimed is:

1. A method of forming a touch fastening material, the method comprising:
   providing a lengthwise-incoherent layer of staple fibers supported directly on a bed of bristle tips of a brush, the total weight of fibers supported on the brush being less than about 40 grams per square meter, including carding staple fibers and then transferring the carded fibers onto the brush;
   needling the layer of staple fibers by cycling fork needles through the layer of staple fibers and into the brush, such that the needles carry loops of fibers of the layer into spaces between bristles of the brush, including penetrating the needles through the layer of fibers to a distance of between 1 and 10 millimeters into the brush with a needling density of between 40 and 320 penetrations per square centimeter; then,
   while the needled layer of staple fibers remains supported on the brush, with the loops of the fibers extending between bristles of the brush, fusing portions of the staple fibers by at least partially melting resin of the fibers disposed outside the brush, by applying heat and pressure to the fibers remaining outside the brush by a surface maintained in contact with the fibers while the fibers are transported by the brush; and then
   pulling the layer of fibers from the brush as a lengthwise-coherent touch fastening material having exposed fastening loops pulled from between the brush bristles;
   wherein the fibers comprise bicomponent fibers including two resins of differing softening temperatures, a plurality of the bicomponent fibers each comprising a core of resin of higher softening temperature than resin of a sheath about the core, and wherein at least partially melting resin of the fibers comprises melting the sheath;
   wherein the fibers have a denier of between about 1 and 20;
   wherein the needling and fusing is performed such that the lengthwise-coherent touch fastening material pulled from the brush has substantially the same overall width as the layer of staple fibers provided on the brush;
   wherein the lengthwise-incoherent layer of staple fibers is continually provided on the brush as a longitudinally continuous layer, and transported by the brush while needled and fused;
   wherein the brush is in the form of a conveyor belt maintained to travel along a linear path during the needling and fusing, and wherein the lengthwise-coherent touch fastening material is pulled from the brush; and
   wherein the lengthwise-incoherent layer of staple fibers is provided supported directly on rounded bristle tips.

2. The method of claim 1, wherein the fibers have a nominal tenacity of at least 1.1 grams per denier.

3. The method of claim 2, wherein the fibers have a nominal tenacity of at least 2.5 grams per denier.

4. The method of claim 1, wherein at least partially melting resin of the fibers comprises melting the sheath of one or more bicomponent fibers, while leaving the core of the bicomponent fibers substantially intact.

5. The method of claim 1, wherein the lengthwise-incoherent layer of staple fibers is transferred onto the brush as a longitudinally continuous layer, such that the fibers are oriented to extend primarily along a length of the layer.

6. The method of claim 1, wherein the lengthwise-incoherent layer of staple fibers is provided supported on a brush having a bristle density of about 380 bristles per square centimeter.

7. The method of claim 1, wherein the lengthwise-incoherent layer of staple fibers is provided supported on bristles having a nominal diameter of between about 4 and 15 times a nominal diameter of the staple fibers.

8. The method of claim 1, wherein fusing portions of the staple fibers comprises fusing such that the lengthwise-coherent touch fastening material as pulled from the brush has a permeability of at least 500 feet3/feet2/sec.

9. The method of claim 1, wherein the needling and fusing is performed such that the lengthwise-coherent touch fastening material pulled from the brush has a fastening surface featuring visually discrete fibers extending between bases of the loops.

10. The method of claim 1, wherein the lengthwise-coherent touch fastening material, as pulled from the brush, consists essentially of material of the layer of staple fibers as provided on the bed of bristle tips of the brush.

* * * * *